United States Patent
Qin

(10) Patent No.: US 12,350,120 B1
(45) Date of Patent: *Jul. 8, 2025

(54) GUM-PROTECTING AND TEETH-WHITENING STRIP AND PREPARATION METHOD THEREOF

(71) Applicant: Jiangxi Dentalbright Technology Co., Ltd., Jiangxi (CN)

(72) Inventor: Junyuan Qin, Jiangxi (CN)

(73) Assignee: Jiangxi Dentalbright Technology Co., Ltd., Jiujiang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/978,002

(22) Filed: Dec. 12, 2024

(30) Foreign Application Priority Data

Nov. 18, 2024 (CN) .......................... 202411648480.2

(51) Int. Cl.
  *A61C 19/06* (2006.01)
  *A61K 8/81* (2006.01)
  *A61Q 11/00* (2006.01)

(52) U.S. Cl.
  CPC .......... *A61C 19/066* (2013.01); *A61K 8/8147* (2013.01); *A61Q 11/00* (2013.01)

(58) Field of Classification Search
  CPC ........... A61K 6/083; A61K 8/84; A61Q 11/00
  USPC ........................................................ 424/49
  See application file for complete search history.

(56) References Cited

U.S. PATENT DOCUMENTS

| | | |
|---|---|---|
| 2006/0024246 A1* | 2/2006 | Maitra ................. A61K 8/8152 424/49 |
| 2024/0108561 A1 | 4/2024 | Strand et al. |
| 2024/0122691 A1 | 4/2024 | Sagel |
| 2024/0139082 A1 | 5/2024 | Ernst |
| 2024/0173217 A1 | 5/2024 | Rajaiah et al. |
| 2024/0173226 A1 | 5/2024 | D'Ambrogio et al. |

FOREIGN PATENT DOCUMENTS

CN 101507688 * 8/2009 ............. A61K 6/083

* cited by examiner

*Primary Examiner* — Walter E Webb
(74) *Attorney, Agent, or Firm* — S.J. Intellectual Property LTD.

(57) ABSTRACT

A teeth-whitening strip includes a soft film layer, a backing layer, and a gel layer positioned therebetween. The gel layer includes the following components by weight: 0.50-30.0 parts of an acrylate copolymer gelling agent for excellent marginal sealing effect, 10.0-50.0 parts of deionized water, 0.10-15.0 parts of a whitening agent, 0.010-2.0 parts of a pH regulator, 0.010-0.30 parts of a sweetener, 0.010-5.0 parts of a desensitizer, 0.0010-0.10 parts of a stabilizer, and 0.050-1.50 parts of a flavoring agent. Its preparation method includes: mixing the above components to obtain a mixture; homogenizing and emulsifying the mixture to obtain a gel; coating the gel on a PET backing film to obtain a paste; baking the paste in an oven; and embossing a PE soft film on a surface of the paste to obtain the gum-protecting and teeth-whitening strip.

18 Claims, No Drawings

GUM-PROTECTING AND TEETH-WHITENING STRIP AND PREPARATION METHOD THEREOF

CROSS REFERENCE TO RELATED APPLICATIONS

This application claims priority benefits to Chinese Patent Application No. 2024116484802, filed on Nov. 18, 2024, the contents of which is incorporated herein by reference.

TECHNICAL FIELD

The present disclosure relates to the technical field of oral care, and in particular, to a residue-free and teeth-whitening strip and its preparation method.

BACKGROUND

As living standards improve, people are becoming increasingly aware of the aesthetics of their teeth. The market is now flooded with a variety of teeth whitening products, such as whitening pens, trays, and strips, all of which are popular among consumer for their whitening effects. Particularly, the whitening strips are favored due to their whitening effects, ease of use, affordability and practicality.

Whitening strips consist of a film layer, an elastic gel layer, and a backing layer. To use, peel off the backing layer and apply the elastic gel layer to the teeth. The gel layer contains whitening agents such as hydrogen peroxide, sodium percarbonate, urea peroxide, and phthalimidoperoxycaproic acid, which release active oxygen to oxidize and break down stains on and/or within the teeth, achieving a bleaching effect. However, these peroxide whitening agents can also irritate oral tissues, causing gum discomfort and even swelling.

To accommodate the various shapes of teeth surfaces, the gel layer of whitening strips must possess sufficient flexibility and plasticity. To ensure the strips adhere to the teeth, most whitening strips on the market typically use flexible gelling agents such as polyvinyl alcohol, cellulose, and polyvinylpyrrolidone. While these flexible gelling agents help the strips adhere to the teeth, their inherently low film-forming strength and poor stability can cause the strips to break easily when removed after use. This leads to gel layer residues remaining on the teeth, a phenomenon commonly referred to as "stuck on the teeth" in the art, affecting user experience and posing safety concerns.

SUMMARY

To address the issue of poor user experience such as gum irritation caused by whitening agents containing peroxide and gel layer residue on the teeth surfaces, the present disclosure provides a gum-protecting and teeth-whitening strip and its preparation method.

To achieve the above aim, a technical solution provided by the embodiments of the present disclosure is as follows.

A first aspect of the present disclosure provides a gum-protecting and teeth-whitening strip, including the following components in parts by weight: 0.50-30.0 parts of an acrylic copolymer gelling agent with marginal sealing effect, 10.0-50.0 parts of deionized water, 0.10-15.0 parts of a whitening agent, 0.010-2.0 parts of a pH regulator, 0.010-0.30 parts of a sweetener, 0.010-5.0 parts of a desensitizer, 0.0010-0.10 parts of a stabilizer, and 0.050-1.50 parts of a flavoring agent.

In some embodiments, the acrylic copolymer gelling agent with marginal sealing effect is prepared by the following steps: adding 500.0 molar parts of deionized water, 6.0 molar parts of trimethylammonium ethyl methacrylate chloride, 0.25 molar parts of polyoxyethylene octylphenol ether (10), 0.15 molar parts of hexadecyltrimethylammonium bromide and 0.15 molar parts of isooctyl thioglycolate into a dry glass reactor sequentially, and mechanically stirring at room temperature for 0.50 hours; heating the glass reactor to a temperature of 65-70° C. at a heating rate of 10° C. per minute; adding 0.050 molar parts of ammonium persulfate into the glass reactor and mechanical stirring for 1.0 hour at 65-70° C.; dropping a mixed solution consisting of 7.0 molar parts of acrylic acid, 5.50 molar parts of lauryl acrylate, 5.50 molar parts of dimethylaminoethyl methacrylate, 3.50 molar parts of ethyl acetoacetate methacrylate, 6.20 molar parts of 2-hydroxypropyl methacrylate and 0.30 molar parts of 4-hydroxybutyl acrylate into the glass reactor within 1.0 hour; adding 0.050 molar parts of ammonium persulfate into the glass reactor and mechanical stirring for 1.0 hour at 65-70° C.; adding 0.020 molar parts of ammonium persulfate into the glass reactor, heating at a heating rate of 10° C. per minute to a temperature of 80-85° C., mechanical stirring at 80-85° C. for 3.0 hours; cooling to room temperature and filtering with a 200-mesh nylon cloth to obtain a filtrate; washing the filtrate with 300.0 molar parts of deionized water 3 times, each time with 100.0 molar parts of deionized water; vacuum drying the filtrate at 60° C. for 48.0 hours; and collecting the acrylic copolymer gelling agent with marginal sealing effect.

In some embodiments, a conductivity of the deionized water is less than 0.01 μS/cm.

In some embodiments, the whitening agent is selected from the group consisting of urea peroxide, phthalimide peroxycaproic acid, sodium phytate and sodium hypochlorite.

In some embodiments, the pH regulator is selected from the group consisting of sodium tripolyphosphate, dipotassium hydrogen phosphate and potassium dihydrogen phosphate.

In some embodiments, the sweetener is licorice extract.

In some embodiments, the desensitizer is selected from the group consisting of potassium nitrate, strontium citrate and hydroxyapatite.

In some embodiments, the stabilizer is selected from the group consisting of ethylenediaminetetraacetic acid, disodium ethylenediaminetetraacetic acid and tartaric acid.

In some embodiments, the flavoring agent is selected from the group consisting of menthol, mint essence, floral essence and fruity essence.

A second aspect of the present disclosure provides a method for preparing a gum-protecting and teeth-whitening strip, including: mixing the acrylic copolymer gelling agent with marginal sealing effect according to claim 2, the deionized water, the whitening agent, the pH regulator, the sweetener, the desensitizer, the stabilizer and the flavoring agent to obtain a mixture; homogenizing and emulsifying the mixture to obtain a gel; coating the gel to a PET backing film to obtain a paste; baking the paste in an oven; and embossing a PE soft film on a surface of the paste to obtain the gum-protecting and teeth-whitening strip.

Compared to the related art, the embodiments of the present disclosure show the beneficial effects as follows. The acrylic copolymer gelling agent with marginal sealing effect, effectively reducing harms to the gums caused by whitening agents containing peroxide. Additionally, it has superior tensile strength and elongation at break, giving the strip an easy-to-peel off and residue-free performance.

Detailed Way

To make the purpose, technical solution and advantages of the present disclosure clearer, the present disclosure will be further described in detail below with reference to the accompanying drawings. The described embodiments shall not be regarded as limitations to the present disclosure. All other embodiments obtained by a person of ordinary skill in the art without creative work are within the protection scope of the present disclosure.

In the following description, "some embodiments" refer to a subset of all possible embodiments, which can be understood that "some embodiments" can represent either the same subset or different subsets of all possible embodiments and they can be combined with each other without conflict. Unless otherwise defined, all technical and scientific terms used in the embodiments of the present disclosure have the same meaning as those generally understood by a person of ordinary skill in the art. The terms used in the embodiments of the present disclosure are only for the purpose of describing but are not intended to limit the present disclosure.

In the following description of the embodiments, the terms "including", "comprising", "having" and "containing" are all open-ended terms, meaning they include but are not limited to.

It should be noted that all raw materials/reagents in the embodiments of the present disclosure can be purchased on the market or prepared according to conventional methods known to a person of ordinary skill in the art. The term "and/or" in the embodiments of the present disclosure is only used to describe the relationship of the associated objects, indicating that there can be three relationships. For example, A and/or B represent three cases: A alone, B alone, and A and B. A and B can be singular or plural, and the character "/" generally indicates that the associated objects before and after are in an "or" relationship.

In the following description of the embodiments, the term "at least one" refers to one or more, and "a plurality of" refers to two or more. "At least one of the following" or similar expressions refer to any combination of these items, including any combination of single or plural items. For example, "at least one of a, b or c", or "at least one of a, b and c", can all represent: a, b, c, a-b (i.e. a and b), a-c, b-c, or a-b-c, in which a, b, c can be single or multiple.

A person of ordinary skill in the art should understand that in the following description of the embodiments of the present disclosure, the order of the serial numbers does not mean the order of execution, and some or all the steps can be executed synchronically or in sequence. The execution order of each process should be determined by its function and internal logic and should not constitute any limitation on the implementation process of the embodiments of the present disclosure.

The terms used in the embodiments of the present disclosure are only for the purpose of describing and are not intended to limit the present disclosure. The singular forms of "a" and "the" used in the embodiments of the present disclosure and the appended claims are also intended to include plural forms, unless the context clearly indicates other meanings.

A person of ordinary skill in the art should understand that the numerical ranges in the embodiments of the present disclosure should be understood as also specifically disclosing each intermediate value between the upper and lower limits of the range. Any stated value, any intermediate value within the stated range, any other stated value, or any smaller range within an intermediate value are also included in the present disclosure. The upper and lower limits of these smaller ranges may be independently included or excluded in the range.

Unless otherwise specified, the technical/scientific terms used herein have the same meanings as commonly understood by a person of ordinary skill in the art. Although the present disclosure only describes some methods and materials, any methods and materials similar or equivalent to those described herein may also be used in the embodiments or test embodiments of the present disclosure. All references mentioned in the present disclosure are generally incorporated to disclose and describe the methods and/or materials related to the references. In the event of a conflict with any incorporated reference, the content of the present disclosure shall prevail.

In a first aspect, the embodiments of the present disclosure provide a gum-protecting whitening strip, which includes the following components in parts by weight: 0.50-30.0 parts of an acrylic copolymer gelling agent with marginal sealing effect, 10.0-50.0 parts of deionized water, 0.10-15.0 parts of a whitening agent, 0.010-2.0 parts of a pH regulator, 0.010-0.30 parts of a sweetener, 0.010-5.0 parts of a desensitizer, 0.0010-0.10 parts of a stabilizer, and 0.050-1.50 parts of a flavoring agent.

In the present disclosure, the acrylic copolymer gelling agent provides excellent sealing effect to the edges of teeth, effectively preventing peroxide whitening agents in the strip from harming the gums. Additionally, it offers superior tensile strength and elongation at break, ensuring the teeth strip have excellent easy-to-peel off and residue-free performance.

In some embodiments, the acrylic copolymer gelling agent with marginal sealing effect is prepared by the following steps: adding 500.0 molar parts of deionized water, 6.0 molar parts of trimethylammonium ethyl methacrylate chloride, 0.25 molar parts of polyoxyethylene octylphenol ether (10), 0.15 molar parts of hexadecyltrimethylammonium bromide and 0.15 molar parts of isooctyl thioglycolate into a dry glass reactor sequentially, and mechanically stirring at room temperature for 0.50 hours; heating the glass reactor to a temperature of 65-70° C. at a heating rate of 10° C. per minute; adding 0.050 molar parts of ammonium persulfate into the glass reactor and mechanical stirring for 1.0 hour at 65-70° C.; dropping a mixed solution consisting of 7.0 molar parts of acrylic acid, 5.50 molar parts of lauryl acrylate, 5.50 molar parts of dimethylaminoethyl methacrylate, 3.50 molar parts of ethyl acetoacetate methacrylate, 6.20 molar parts of 2-hydroxypropyl methacrylate and 0.30 molar parts of 4-hydroxybutyl acrylate into the glass reactor within 1.0 hour; adding 0.050 molar parts of ammonium persulfate into the glass reactor, mechanical stirring for 1.0 hour at 65-70° C.; adding 0.020 molar parts of ammonium persulfate into the glass reactor, heating at a heating rate of 10° C. per minute to a temperature of 80-85° C., mechanical stirring at 80-85° C. for 3.0 hours; cooling to room temperature and filtering with a 200-mesh nylon cloth to obtain a filtrate; washing the filtrate with 300.0 molar parts of deionized water 3 times, each time with 100.0 molar parts of deionized water; vacuum drying the filtrate at 60° C. for 48.0 hours; and collecting the acrylic copolymer gelling agent with marginal sealing effect.

It should be noted that the structural formula of the acrylic copolymer gelling agent with marginal sealing effect is as follows.

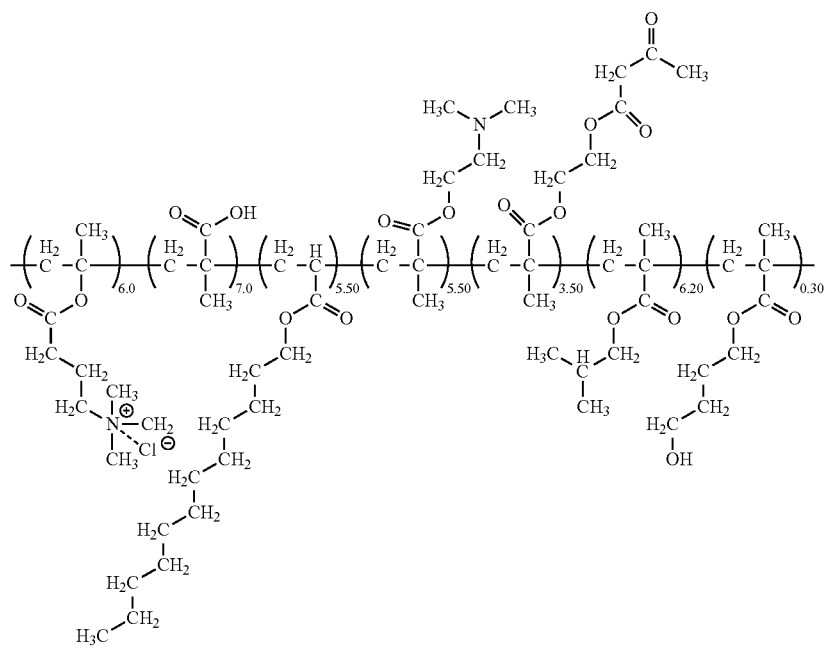

In some embodiments, the conductivity of the deionized water is less than 0.01 μS/cm.

It should be noted that the deionized water acts as a solvent to increase the solubility of the acrylic copolymer gelling agent with marginal sealing effect and ensure that the acrylic copolymer gelling agent with marginal sealing effect is completely dissolved.

In some embodiments, the whitening agent is selected from the group consisting of urea peroxide, phthalimide peroxycaproic acid, sodium phytate and sodium hypochlorite.

It should be noted that the whitening agent whitens the teeth by removing stains physically and through chemical oxidation, improving the whiteness of the tooth surface.

In some embodiments, the pH regulator is selected from the group consisting of sodium tripolyphosphate, dipotassium hydrogen phosphate and potassium dihydrogen phosphate.

It should be noted that the pH regulator plays a role in stabilizing the distribution of components, avoiding distribution changes due to surface segregation effects, which could affect the teeth whitening efficacy.

In some embodiments, the sweetener a licorice extract, and the glycyrrhizic acid content is not less than 12%.

It should be noted that the sweetener plays a role in increasing the sweetness of the gel layer and improving the user experience.

In some embodiments, the desensitizer is selected from the group consisting of potassium nitrate, strontium citrate and hydroxyapatite.

It should be noted that the desensitizer plays a desensitizing role to reduce allergic reactions in users.

In some embodiments, the stabilizer is selected from the group consisting of ethylenediaminetetraacetic acid, disodium ethylenediaminetetraacetic acid or tartaric acid.

It should be noted that the stabilizer plays a role in stabilizing the whitening agent, preventing the whitening agent from decomposed during storage, which may affect the whitening efficacy.

In some embodiments, the flavoring agent is selected from the group consisting of menthol, mint essence, floral essence or fruity essence.

It should be noted that the flavoring agent plays a role in regulating the fragrance of the gel layer, providing users with more fragrance options.

In a second aspect, the embodiments of the present disclosure provide a method for preparing the gum-protecting and teeth-whitening strip described in the first aspect, the preparation method includes the following steps: mixing the acrylic copolymer gelling agent with marginal sealing effect according to claim 2, the deionized water, the whitening agent, the pH regulator, the sweetener, the desensitizer, the stabilizer and the flavoring agent to obtain a mixture; homogenizing and emulsifying the mixture to obtain a gel; coating the gel to a PET backing film to obtain a paste; baking the paste in an oven; and embossing a PE soft film on a surface of the paste to obtain the gum-protecting and teeth-whitening strip.

It should be noted that the gum-protecting and teeth-whitening strip is prepared by the following steps: adding 0.50-30.0 parts of acrylic copolymer gelling agent with marginal sealing effect, 10.0-50.0 parts of deionized water, 0.10-15.0 parts of whitening agent, 0.010-2.0 parts of pH adjusting agent, 0.010-0.30 parts of sweetener, 0.010-5.0 parts of desensitizer, 0.0010-0.10 parts of stabilizer, and 0.050-1.50 parts of flavoring agent into a vacuum homogenizing emulsifier for homogenizing and emulsifying at 25-30° C. and 0.1 MPa for 2.0 hours to obtain a gel, and coated the gel evenly on a PET film substrate by a coating machine to obtain a paste, placing the paste in a baking oven at 60° C. for 0.5 hours, and then embossing and covering a PE soft film on a surface of the gel layer of the paste by a three-roll calender to obtain the gum-protecting and teeth-whitening strip.

The technical method of the present disclosure will be further described in conjunction with the embodiments below.

EXAMPLE 1

This example 1 provides a method for preparing a gum-protecting and teeth-whitening strip 1, and the steps are as follows.

1) Preparation of an acrylic copolymer gelling agent 1 with marginal sealing effect: 500.0 molar parts of deionized water, 6.0 molar parts of trimethylammonium ethyl methacrylate chloride, 0.25 molar parts of polyoxyethylene octylphenol ether (10) (OP-10), 0.15 molar parts of hexadecyltrimethylammonium bromide and 0.15 molar parts of isooctyl thioglycolate were added into a dry glass reactor in sequence and then be stirred mechanically at room temperature for 0.50 hours; the glass reactor was heated to 65° C. at a heating rate of 10° C. per minute; 0.050 molar parts of ammonium persulfate was added and mechanically stirred at the temperature of 65° C. for 1.0 hour; a mixed solution consisting of 7.0 molar parts of acrylic acid, 5.50 molar parts of lauryl acrylate, 5.50 molar parts of dimethylaminoethyl methacrylate, 3.50 molar parts of ethyl acetoacetate methacrylate, 6.20 molar parts of 2-hydroxypropyl methacrylate and 0.30 molar parts of 4-hydroxybutyl acrylate was dropped into the glass reactor within 1.0 hour; 0.050 molar parts of ammonium persulfate was added and mechanically stirred at the temperature of 65° C. for 1.0 hour; 0.020 molar parts of ammonium persulfate was added; the glass reactor was heated to 80° C. at a heating rate of 10° C. per minute; the temperature was kept at 80° C. for reaction by mechanical stirring for 3.0 hours; the glass reactor was cooled to room temperature; the mixture was filtered with a 200-mesh nylon cloth to discharge a filtrate; the filtrate was washed with 300.0 molar parts of deionized water 3 times, each time with 100.0 molar parts; and then the filtrate was heated at 60° C. for vacuum drying for 48.0 hours to obtain the acrylic copolymer gelling agent 1 with marginal sealing effect.

2) Preparation of the gum-protecting and teeth-whitening strip 1:0.5 parts of acrylic copolymer gelling agent 1 with marginal sealing effect, 10.0 parts of deionized water, 0.10 parts of urea peroxide, 0.010 parts of sodium tripolyphosphate, 0.010 parts of licorice extract, 0.010 parts of potassium nitrate, 0.0010 parts of ethylenediaminetetraacetic acid, and 0.050 parts of menthol were added into a homogenizing emulsifier for homogenizing and emulsifying at 25° C. for 2.0 hours to obtain a gel; the gel was evenly coated on a PET backing film by a coating machine to obtain a paste; the paste was placed in an oven for baking at 60° C. for 0.5 hours; a PE soft film was embossed and covered on a surface of the gel layer of the paste by a three-roll calender to obtain a gum-protecting and teeth-whitening strip 1.

EXAMPLE 2

Example 2 provides a method for preparing a gum-protecting and teeth-whitening strip 2, and the steps are as follows.

1) Preparation of an acrylic copolymer gelling agent 2 with marginal sealing effect: 500.0 molar parts of deionized water, 6.0 molar parts of trimethylammonium ethyl methacrylate chloride, 0.25 molar parts of OP-10, 0.15 molar parts of hexadecyltrimethylammonium bromide and 0.15 molar parts of isooctyl thioglycolate were added into a dry glass reactor in sequence and stirred mechanically at room temperature for 0.50 hours; the glass reactor was heated to 70° C. at a heating rate of 10° C. per minute; 0.050 molar parts of ammonium persulfate was added; the temperature at 70° C. was kept for reaction by mechanical stirring for 1.0 hour; a mixed solution consisting of 7.0 molar parts of acrylic acid, 5.50 molar parts of lauryl acrylate, 5.50 molar parts of dimethylaminoethyl methacrylate, 3.50 molar parts of ethyl acetoacetate methacrylate, 6.20 molar parts of 2-hydroxypropyl methacrylate and 0.30 molar parts of 4-hydroxybutyl acrylate was dropped into the glass reactor within 1.0 hour; 0.050 molar parts of ammonium persulfate was added for reaction at the temperature of 70° C. for 1.0 hour with mechanical stirring; 0.020 molar parts of ammonium persulfate was added; the glass reactor was heated to 85° C. at a heating rate of 10° C. per minute; the temperature was kept at 85° C. for 3.0 hours with mechanical stirring; the glass reactor was cooled to room temperature; the mixture was filtered with a 200-mesh nylon cloth to discharge a filtrate; the filtrate was washed with 300.0 molar parts of deionized water 3 times, with 100.0 molar parts each time; and then the filtrate was heated at 60° C. for vacuum drying for 48.0 hours to obtain the acrylic copolymer gelling agent 2 with marginal sealing effect.

2) Preparation of the gum-protecting and teeth-whitening strip 2: 30.0 parts of acrylic copolymer gelling agent 2 with marginal sealing effect, 50.0 parts of deionized water, 15.0 parts of urea peroxide, 2.0 parts of sodium tripolyphosphate, 0.30 parts of licorice extract, 5.0 parts of potassium nitrate, 0.10 parts of ethylenediaminetetraacetic acid, and 1.50 parts of menthol were added to a homogenizing emulsifier for homogenizing and emulsifying at 30° C. for 2.0 hours to obtain a gel; the gel was evenly coated on a PET film substrate by a coating machine to obtain a paste; the paste was placed in a baking oven at 60° C. for 0.5 hours; then a PE soft film was embossed and covered on a surface of the gel layer of the paste by a three-roll calender to obtain the gum-protecting and teeth-whitening strip 2.

COMPARATIVE EXAMPLE 1

Comparative example 1 provides a method for preparing a teeth-whitening strip 3, and the steps are as follows.

0.5 parts of a polyvinyl alcohol gelling agent with a viscosity of 70.0 mpas, 2.0 parts of polyvinyl pyrrolidone, 0.1 parts of sodium cellulose, 10.0 parts of medical alcohol, 10.0 parts of deionized water, 0.5 parts of glycerol, 0.1 parts of urea peroxide, 0.01 parts of sodium tripolyphosphate, 0.01 parts of sucralose, 0.01 parts of citric acid, 0.01 parts of potassium nitrate, 0.001 parts of ethylenediaminetetraacetic acid, and 0.05 parts of menthol were added into a vacuum homogenizing emulsifier for homogenizing and emulsifying at 25° C. and 0.1 MPa for 2.0 hours to obtain a gel; the gel was coated on a PET film by a coating machine to obtain a paste; the paste was placed in an oven at 60° C. for baking for 3.0 hours; and then a PE soft film was embossed on a surface of the gel layer of the paste by a three-roll calender to obtain the teeth-whitening strip 3.

COMPARATIVE EXAMPLE 2

Comparative example 2 provides a preparation method of a teeth-whitening strip 4, and the steps are as follows.

50.0 parts of polyvinyl pyrrolidone, 15.0 parts of sodium cellulose, 50.0 parts of medical alcohol, 50.0 parts of deionized water, 15.0 parts of glycerol, 15.0 parts of urea peroxide, 2.0 parts of sodium tripolyphosphate, 0.30 parts of sucralose, 0.40 parts of citric acid, 5.0 parts of potassium nitrate, 0.10 parts of ethylenediaminetetraacetic acid, and 1.50 parts of menthol was added into a vacuum homogenizing emulsifier for homogenizing and emulsifying at 30° C. and 0.1 MPa for 2.0 hours to obtain a gel; the gel was evenly coated on a PET film substrate by a coating machine to obtain a paste; the paste was placed in an oven for 3.0 hours; and a PE soft film was embossed on a surface of the gel layer of the paste by a three-roll calender to obtain the teeth-whitening strip 4.

Performance Test

Test 1: Gum Protection

Test conditions are as follows: Using Shandong Sairuite SRT-Z029 periodontal probe torque tester, the gum conditions of each group of 50 healthy volunteers were assessed after applying the gum-protecting and teeth-whitening strips. The teeth strips were applied twice daily, once from 9:00 to 9:30 and once from 15:00 to 15:30, for 7 consecutive days. Periodontal probing was conducted afterward. The test results are shown in Table 1.

Test 2: Strength

Test conditions are as follows: Shanghai Hengyi tensile testing machine (HY 0580 (DB)) was used for measurement. At room temperature, a teeth strip sample with the back layer removed was clamped between an upper clamp and a lower clamp and subjected to tensile testing under set conditions. The initial effective length between the two clamps was 40 mm, and the moving speed of the clamps was 100 m/min. The tensile strength, or the tensile strength at break was determined based on the tensile force at final break and the initial cross-sectional dimension of the sample. The elongation at break was calculated by subtracting the initial effective length of the sample between the two clamps from the maximum tensile length of the sample between the two clamps, then dividing by the initial effective length of the sample between the two clamps. The test was performed 10 times, and the average value was taken. The test results are shown in Table 1.

Test 3: Breakage

The teeth-whitening strips from the above examples and comparative examples were tested in practical applications after removing the backing layer. The strips were attached to the teeth surface and peeled off after 15 minutes, whether there was any residue or breakage was recorded. Each sample group was tested 10 times, and the average value was taken. The test results are shown in Table 1.

Test 4: Release Rate of Whitening Agent

In an indoor environment with a temperature of 25° C., a teeth-whitening strip was pasted on a glass slide and then immersed in a beaker containing 1 L of deionized water, and the glass slide was arranged parallel to the wall of the beaker. The change of peroxide concentration in water was monitored from the beginning of sample immersion, and the concentration was measured at 10 minutes, 30 minutes, and 1 hour using an RQflex reflectometer. After 1 hour, the teeth-whitening strip was dissolved in ethyl acetate, and then the dissolved teeth strip was added to a beaker containing 1 L of deionized water, stirred evenly, and the total concentration of the whitening component (peroxide) in the teeth strip was measured. The concentration dissolution rate (the value of the peroxide concentration in the water to the total concentration) at each measurement time point was calculated.

Test 5: Whitening Effect

Maxillary premolars extracted within the past 30 days for orthodontic reasons were selected, and the tooth surface color difference (L* value) was measured using a spectral colorimeter. The teeth were then wrapped with whitening strips and immersed in a beaker containing 100 ml of deionized water at 37° C. for 2.0 hours. After removing the whitening strips, the tooth surface color difference (L* value) was measured again with the spectral colorimeter. The whitening effect was evaluated based on the change in L* value (ΔL) before and after the immersion treatment.

The test results are shown in Table 1:

TABLE 1

Teeth-whitening strip performance test results.

| Sample | Tensile Strength/MPa | Elongation at break/% | Number of people experiencing symptoms such as gum swelling, pain, bleeding, bad breath, and loose tooth. | Breakage and residue on the tooth surface | Whitening agent dissolution rate/% | | | ΔL |
|---|---|---|---|---|---|---|---|---|
| | | | | | 10 min | 30 min | 60 min | |
| Example 1 | 5.73 | 612 | 0 | No | 63.5 | 79.5 | 90.5 | 9.78 |
| Example 2 | 5.96 | 635 | 0 | No | 62.2 | 83.6 | 94.5 | 9.69 |
| Comparative Example 1 | 1.46 | 467 | 4 | Yes | 54.2 | 83.1 | 88.6 | 7.12 |
| Comparative Example 2 | 2.15 | 378 | 3 | Yes | 49.5 | 75.2 | 88.5 | 6.63 |

The test results indicate that the number of people experiencing symptoms such as gum swelling, pain, bleeding, bad breath, and loose tooth in Examples 1 and 2 was significantly lower than in Comparative Examples 1-2, demonstrating the superior gum protection effect of the strips. Additionally, Examples 1 and 2 showed no breakage or residue upon removal, unlike Comparative Examples 1 and 2, which showed breakage and residue. Comparative Example 2 also exhibited poor plasticity and adhesion to the tooth surface, indicating that the whitening strips from Examples 1 and 2 have excellent residue-free performance. Furthermore, the dissolution rate of the whitening agents in Examples 1 and 2 increased evenly, indicating excellent sustained whitening performance. Finally, the whitening effect of the strips in Example 1 and 2 was significantly higher than that of Comparative Example 1 and 2.

The above are only specific embodiments of the present disclosure, but the protection scope of the present disclosure is not limited thereto. A person of ordinary skill in the art can easily think of changes or substitutions within the technical scope disclosed in the present disclosure and should be covered by the protection scope of the present disclosure.

Therefore, the protection scope of the present disclosure should be subject to the protection scope of the claims.

What is claimed is:

1. A gum-protecting and teeth-whitening strip, comprising the following components in parts by weight:
0.50-30.0 parts of an acrylic copolymer gelling agent with marginal sealing effect, 10.0-50.0 parts of deionized water, 0.10-15.0 parts of a whitening agent, 0.010-2.0 parts of a pH regulator, 0.010-0.30 parts of a sweetener, 0.010-5.0 parts of a desensitizer, 0.0010-0.10 parts of a stabilizer, and 0.050-1.50 parts of a flavoring agent.

2. The gum-protecting and teeth-whitening strip according to claim 1, wherein the acrylic copolymer gelling agent with marginal sealing effect is prepared by the following steps:
adding 500.0 molar parts of deionized water, 6.0 molar parts of trimethylammonium ethyl methacrylate chloride, 0.25 molar parts of polyoxyethylene octylphenol ether (10), 0.15 molar parts of hexadecyltrimethylammonium bromide and 0.15 molar parts of isooctyl thioglycolate into a dry glass reactor sequentially, and mechanically stirring at room temperature for 0.50 hours;
heating the glass reactor to a temperature of 65-70° C. at a heating rate of 10° C. per minute;
adding 0.050 molar parts of ammonium persulfate into the glass reactor and mechanical stirring for 1.0 hour at 65-70° C.;
dropping a mixed solution consisting of 7.0 molar parts of acrylic acid, 5.50 molar parts of lauryl acrylate, 5.50 molar parts of dimethylaminoethyl methacrylate, 3.50 molar parts of ethyl acetoacetate methacrylate, 6.20 molar parts of 2-hydroxypropyl methacrylate and 0.30 molar parts of 4-hydroxybutyl acrylate into the glass reactor within 1.0 hour;
adding 0.050 molar parts of ammonium persulfate into the glass reactor and mechanical stirring for 1.0 hour at 65-70° C.;
adding 0.020 molar parts of ammonium persulfate into the glass reactor, heating at a heating rate of 10° C. per minute to a temperature of 80-85° C., and mechanical stirring at 80-85° C. for 3.0 hours;
cooling to room temperature and filtering with a 200-mesh nylon cloth to obtain a filtrate;
washing the filtrate with 300.0 molar parts of deionized water 3 times, each time with 100.0 molar parts of deionized water;
vacuum drying the filtrate at 60° C. for 48.0 hours; and
collecting the acrylic copolymer gelling agent with marginal sealing effect.

3. The gum-protecting and teeth-whitening strip according to claim 1, wherein a conductivity of the deionized water is less than 0.01 pS/cm.

4. The gum-protecting and teeth-whitening strip according to claim 1, wherein the whitening agent is selected from the group consisting of urea peroxide, phthalimide peroxycaproic acid, sodium phytate and sodium hypochlorite.

5. The gum-protecting and teeth-whitening strip according to claim 1, wherein the pH regulator is selected from the group consisting of sodium tripolyphosphate, dipotassium hydrogen phosphate and potassium dihydrogen phosphate.

6. The gum-protecting and teeth-whitening strip according to claim 1, wherein the sweetener is licorice extract.

7. The gum-protecting and teeth-whitening strip according to claim 1, wherein the desensitizer is selected from the group consisting of potassium nitrate, strontium citrate and hydroxyapatite.

8. The gum-protecting and teeth-whitening strip according to claim 1, wherein the stabilizer is selected from the group consisting of ethylenediaminetetraacetic acid, disodium ethylenediaminetetraacetic acid and tartaric acid.

9. The gum-protecting and teeth-whitening strip according to claim 1, wherein the flavoring agent is selected from the group consisting of menthol, mint essence, floral essence and fruity essence.

10. A method for preparing a gum-protecting and teeth-whitening strip, comprising the following steps:
mixing 0.50-30.0 parts of an acrylic copolymer gelling agent with marginal sealing effect, 10.0-50.0 parts of deionized water, 0.10-15.0 parts of a whitening agent, 0.010-2.0 parts of a pH regulator, 0.010-0.30 parts of a sweetener, 0.010-5.0 parts of a desensitizer, 0.0010-0.10 parts of a stabilizer, and 0.050-1.50 parts of a flavoring agent to obtain a mixture;
homogenizing and emulsifying the mixture to obtain a gel;
coating the gel on a PET backing film to obtain a paste;
baking the paste in an oven; and
embossing a PE soft film on a surface of the paste to obtain the gum-protecting and teeth-whitening strip.

11. The method according to claim 10, wherein the acrylic copolymer gelling agent is prepared by the following steps:
adding 500.0 molar parts of deionized water, 6.0 molar parts of trimethylammonium ethyl methacrylate chloride, 0.25 molar parts of polyoxyethylene octylphenol ether (10), 0.15 molar parts of hexadecyltrimethylammonium bromide and 0.15 molar parts of isooctyl thioglycolate into a dry glass reactor sequentially, and mechanically stirring at room temperature for 0.50 hours;
heating the glass reactor to a temperature of 65-70° C. at a heating rate of 10° C. per minute;
adding 0.050 molar parts of ammonium persulfate into the glass reactor and mechanical stirring for 1.0 hour at 65-70° C.;
dropping a mixed solution consisting of 7.0 molar parts of acrylic acid, 5.50 molar parts of lauryl acrylate, 5.50 molar parts of dimethylaminoethyl methacrylate, 3.50 molar parts of ethyl acetoacetate methacrylate, 6.20 molar parts of 2-hydroxypropyl methacrylate and 0.30 molar parts of 4-hydroxybutyl acrylate into the glass reactor within 1.0 hour;
adding 0.050 molar parts of ammonium persulfate into the glass reactor and mechanical stirring for 1.0 hour at 65-70° C.;
adding 0.020 molar parts of ammonium persulfate into the glass reactor, heating at a heating rate of 10° C. per minute to a temperature of 80-85° C., and mechanical stirring at 80-85° C. for 3.0 hours;
cooling to room temperature and filtering with a 200-mesh nylon cloth to obtain a filtrate;
washing the filtrate with 300.0 molar parts of deionized water 3 times, each time with 100.0 molar parts of deionized water;
vacuum drying the filtrate at 60° C. for 48.0 hours; and
collecting the acrylic copolymer gelling agent.

12. The method according to claim 10, wherein a conductivity of the deionized water is less than 0.01 μS/cm.

13. The method according to claim 10, wherein the whitening agent is selected from the group consisting of urea peroxide, phthalimide peroxycaproic acid, sodium phytate and sodium hypochlorite.

14. The method according to claim 10, wherein the pH regulator is selected from the group consisting of sodium tripolyphosphate, dipotassium hydrogen phosphate and potassium dihydrogen phosphate.

15. The method according to claim 10, wherein the sweetener is licorice extract.

16. The method according to claim 10, wherein the desensitizer is selected from the group consisting of potassium nitrate, strontium citrate and hydroxyapatite.

17. The method according to claim 10, wherein the stabilizer is selected from the group consisting of ethylenediaminetetraacetic acid, disodium ethylenediaminetetraacetic acid and tartaric acid.

18. The method according to claim 10, wherein the flavoring agent is selected from the group consisting of menthol, mint essence, floral essence and fruity essence.

* * * * *